United States Patent
Stierstorfer

(10) Patent No.: US 7,391,927 B2
(45) Date of Patent: Jun. 24, 2008

(54) METHOD FOR REMOVING RING ARTIFACTS FROM TOMOGRAMS PRODUCED WITH THE AID OF A COMPUTED TOMOGRAPHY UNIT

(75) Inventor: Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 456 days.

(21) Appl. No.: 11/225,035

(22) Filed: Sep. 14, 2005

(65) Prior Publication Data

US 2006/0056579 A1 Mar. 16, 2006

(30) Foreign Application Priority Data

Sep. 15, 2004 (DE) ................ 10 2004 044 698

(51) Int. Cl.
 *G06K 9/40* (2006.01)
(52) U.S. Cl. .................. 382/275; 382/128; 382/131; 382/274
(58) Field of Classification Search ............... 382/128, 382/130, 131, 260, 274, 275
See application file for complete search history.

(56) References Cited

U.S. PATENT DOCUMENTS

| | | | |
|---|---|---|---|
| 5,127,037 A * | 6/1992 | Bynum ..................... 378/4 |
| 5,644,610 A * | 7/1997 | Crawford et al. ............. 378/19 |
| 5,867,554 A | 2/1999 | Hupke | |
| 6,031,374 A * | 2/2000 | Epstein et al. ............. 324/306 |
| 6,047,039 A | 4/2000 | Flohr | |
| 6,448,559 B1 * | 9/2002 | Saoudi et al. .............. 250/367 |
| 7,053,376 B2 * | 5/2006 | Amemiya et al. ...... 250/363.04 |

FOREIGN PATENT DOCUMENTS

DE 198 35 451 A1 3/1999
EP 0 819 406 A1 1/1998

* cited by examiner

*Primary Examiner*—Yosef Kassa
(74) *Attorney, Agent, or Firm*—Harness, Dickey & Pierce, P.L.C.

(57) ABSTRACT

A method and a computed tomography unit are disclosed, that render it possible in a simple way to remove ring artifacts from tomograms $I_k$, particularly in the case of a fast feed of the recording region per revolution of the recording system of the computed tomography unit by calculating a ring artifact image $I_k$ for each tomogram $I_k$. In this procedure, temporary ring artifact images $Rt_k$ are firstly calculated for each tomogram $I_k$, and subsequently the final ring artifact image $R_k$ is formed for the purpose of correcting the respective tomogram $I_k$ by averaging over at least a portion $T_{sub}$ of the temporary ring artifact images $Rt_k$, the temporary ring artifact images $Rt_k$ being rotated before averaging in such a way that the ring artifacts present in the temporary artifact images $Rt_k$ substantially coincide and their position substantially corresponds to the ring artifacts present in the tomogram $I_k$.

20 Claims, 3 Drawing Sheets

_US 7,391,927 B2_

METHOD FOR REMOVING RING ARTIFACTS FROM TOMOGRAMS PRODUCED WITH THE AID OF A COMPUTED TOMOGRAPHY UNIT

The present application hereby claims priority under 35 U.S.C. §119 on German patent application number DE 10 2004 044 698.9 filed Sep. 15, 2004, the entire contents of which is hereby incorporated herein by reference.

FIELD

The invention generally relates to a method for removing ring artifacts from tomograms produced with the aid of a computed tomography unit, and/or to a computed tomography unit, such as one operating according to such a method for example.

BACKGROUND

The recording system of a computed tomography unit which is known, for example, from EP 0 819 406 A1 includes an X-ray machine and a multirow detector. An X-ray machine and detector are arranged lying opposite one another on a rotary frame such that an object volume in the form of a spiral scan can be scanned during rotation of the rotary frame about a rotation axis and during a continuous feed of the object, which is supported on a bearing frame, in the direction of the rotation axis. A tomogram or volumetric image is reconstructed on the basis of the X-ray images acquired by the detector during the spiral scan from different projection directions.

Ring artifacts that are centered about a center of rotation, identifiable in the tomogram, of the recording system of the computed tomography unit cause signal errors of individual detector elements of the multirow detector. DE 198 35 451 A1 describes a method for removing ring artifacts in tomograms produced with the aid of a computed tomography unit. The known method includes method steps for calculating a correction image that substantially includes only the ring artifacts present in the tomogram.

The tomogram is subjected to at least one instance of median filtering for this purpose. An instance of low-pass filtering following thereupon serves the purpose of suppressing interfering noise components and noise structures. The low-pass filtering is performed along circular arcs about the center of rotation in the image. In the case of the known method, a result image in which the ring artifacts are suppressed is produced by a subsequent subtraction of the low-pass-filtered correction image from the input image, it being necessary, however, for the ring artifacts to have a certain minimum length for a successful suppression.

The length of a ring artifact or of a ring segment representing a ring artifact is determined by the speed with which that recording region of an object which is to be scanned is displaced in the direction of the rotation axis during each revolution of the recording system. The ring segment becomes shorter in this case the quicker the feed of the recording region to be scanned. However, ring segments of a short length such as are produced during rapid scanning of the recording region are not acquired or suppressed at all in tomograms in the case of the known method, or only unsatisfactorily so.

SUMMARY

An object of at least one embodiment of the present invention is to specify a method with the aid of which an improved removal of ring artifacts in tomograms is possible in a simple way.

An object may be achieved by a method for removing ring artifacts from tomograms, and/or by way of a computed tomography unit, such as one operating according to such a method for example.

According to at least one embodiment of the invention, a method for removing ring artifacts includes reconstructing tomograms $I_k$ at recording positions ($k=1, \ldots, N$) that are substantially equidistant in the direction of a rotation axis of the computed tomography unit, and calculating a temporary ring artifact image $Rt_k$ for each tomogram $I_k$ which has at least one ring artifact present in the respective tomogram $I_k$. The method further includes method steps for calculating a ring artifact image $R_k$ for each tomogram, the respective ring artifact image $R_k$ being formed by averaging over at least a portion of the temporary ring artifact images $Rt_k$, and the temporary ring artifact images $Rt_k$ being rotated before averaging in such a way that the ring artifacts present in the temporary artifact images $Rt_k$ substantially coincide and their position substantially corresponds to the ring artifacts present in the tomogram $I_k$. In addition, a method step is included for subtracting the respective ring artifact image $R_k$ from the respective tomogram $I_k$, at least one result image $E_k$ being produced in which the ring artifact is removed.

At least one embodiment of the invention proceeds from the fundamental finding that ring artifacts in consecutive tomograms that are acquired substantially at equidistant recording positions and under the same scanning conditions are of the same shape but are rotated by an angle to one another about a respective center of rotation of the tomogram. In addition to the ring artifacts present in a respective tomogram, the temporary ring artifact images that can be calculated for each tomogram can also have additional image perturbations such as pixel noise, for example. The correction of the ring artifacts in a tomogram is not performed, as previously, on the basis of an individual image, but on the basis of an averaging over a portion of the temporary ring artifact images obtained at various recording positions, such that the image perturbations present in the respective temporary ring artifact image are suppressed by a low-pass effect. In order for the ring artifacts present in the temporary ring artifact images to coincide, the temporary ring artifact images are rotated with reference to the tomogram to be corrected.

By contrast with the known method, at least one embodiment of the invention therefore includes low-pass filtering in the time domain on the basis of images that have been acquired at different recording positions and/or at different times. In addition, interfering noise structures and interfering pixel noise are removed independently of the length of a ring artifact that is present.

According to an advantageous refinement of at least one embodiment of the invention, calculation of the temporary ring artifact image may be performed using the following method steps:

b1) masking bone and air fractions in the respective tomogram $I_k$ such that a masked image $N_k$ is respectively produced for each tomogram $I_k$, b2) subjecting the respective masked image $N_k$ to high-pass filtering in the radial direction relative to the center of rotation in the masked image $N_k$ such that a high-pass-filtered image $H_k$ is produced for each masked image $N_k$, and b3) artifact threshold value formation in the respective high-pass-filtered image $H_k$ with a negative artifact threshold and a positive artifact threshold, so as to produce for each high-pass-filtered image $H_k$ the temporary ring artifact image $Rt_k$ that has the ring artifacts present in the respective tomogram $I_k$.

Masking of bone and air fractions may be performed advantageously by way of the following method steps:

b11) all the values greater than an upper threshold SWO are set equal to SWO, and b2) all the image values smaller than a lower threshold SWU are set equal to SWU such that a masked image $N_k$ is produced.

The high-pass filtering of the respective masked image may further include, for example, the following method steps:

b21) carrying out median filtering in radial directions, running through the center of rotation ($D_z$), in the masked image $N_k$ such that a median-filtered image $M_k$ is produced, and b22) subtracting the median-filtered image $M_k$ from the tomogram $I_k$ such that a high-pass-filtered image $H_k$ is produced.

The temporary ring artifact images $Rt_k$ contain not only ring artifacts, but also noise structures of object parts that have been falsely recognized as artifacts. These noise structures can preferably be eliminated by means of low-pass filtering in the respective temporary ring artifact image $Rt_k$ in the azimuth direction along at least one circular segment. In this case, the circular segments correspond to a part of a circle seated at the center of rotation, the circular segments covering, for example, an angular range of 10 degrees of a complete circle and being matched to the respective length of the ring artifact.

On the basis of the temporary ring artifact images $Rt_k$ thus determined, the ring artifact image $R_k$ used for correcting the ring artifacts is preferably calculated for the respective input image using the following rule:

$$R_k = \sum_{l=-T}^{+T} w_l \cdot Rot_{l \cdot \delta}(Rt_{l+k}),$$

where l is an index traversing the values $-T$ and $+T$, $w_1$ is a weighting factor dependent on the index l, $\delta$ is the angular spacing of ring artifacts between two neighboring tomograms, and Rot is a rotation operator that rotates the temporary ring artifact image $Rt_{1+k}$ by the angle $l*\delta$ about the center of rotation, the following relationships holding:

$$T_{sub} = 2*T+1, \quad \sum_{l=-T}^{T} w_l = 1 \quad \text{and} \quad \delta = 2*\pi*d/V,$$

and d corresponding to a difference between the neighboring recording positions and V corresponding to feed of the recording system in the direction of the system axis.

The weighting factors $w_1$, which are each multiplied in accordance with the abovenamed calculation rule by the respective rotated temporary ring artifact image $Rt_k$, take the following form:

$$w_1 = 1/T_{sub}.$$

However, it is also possible to use any other desired weighting factors such that low-pass filtering can be performed with the aid of a characteristic matched to the situation. All that is essential is that the sum of all the coefficients yields 1.

Instead of low-pass filtering in the respective temporary ring artifact image $Rt_k$, it is also possible to carry out low-pass filtering of the calculated final ring artifact image $R_k$. The low-pass filtering in the ring artifact image $R_k$ in the azimuth direction is performed, again preferably, along at least one circular segment that corresponds to a part of a circle seated at the center of rotation and which has a circular segment length matched to the ring artifact. The circular segment length can, for example, cover an angular range of 10 degrees of a complete circle.

In an advantageous refinement of at least one embodiment of the invention, at least one method step is carried out in polar coordinates with an origin of coordinates seated at the center of rotation of the image.

According to at least one embodiment of the invention, a computed tomography unit is configured in such a way that it is possible to execute the method according to at least one embodiment of the invention for removing ring artifacts.

BRIEF DESCRIPTION OF THE DRAWINGS

Example embodiments and further advantageous refinements of the invention are illustrated in the following schematic drawings, in which.

DETAILED DESCRIPTION OF THE EXAMPLE EMBODIMENTS

Figure 1:
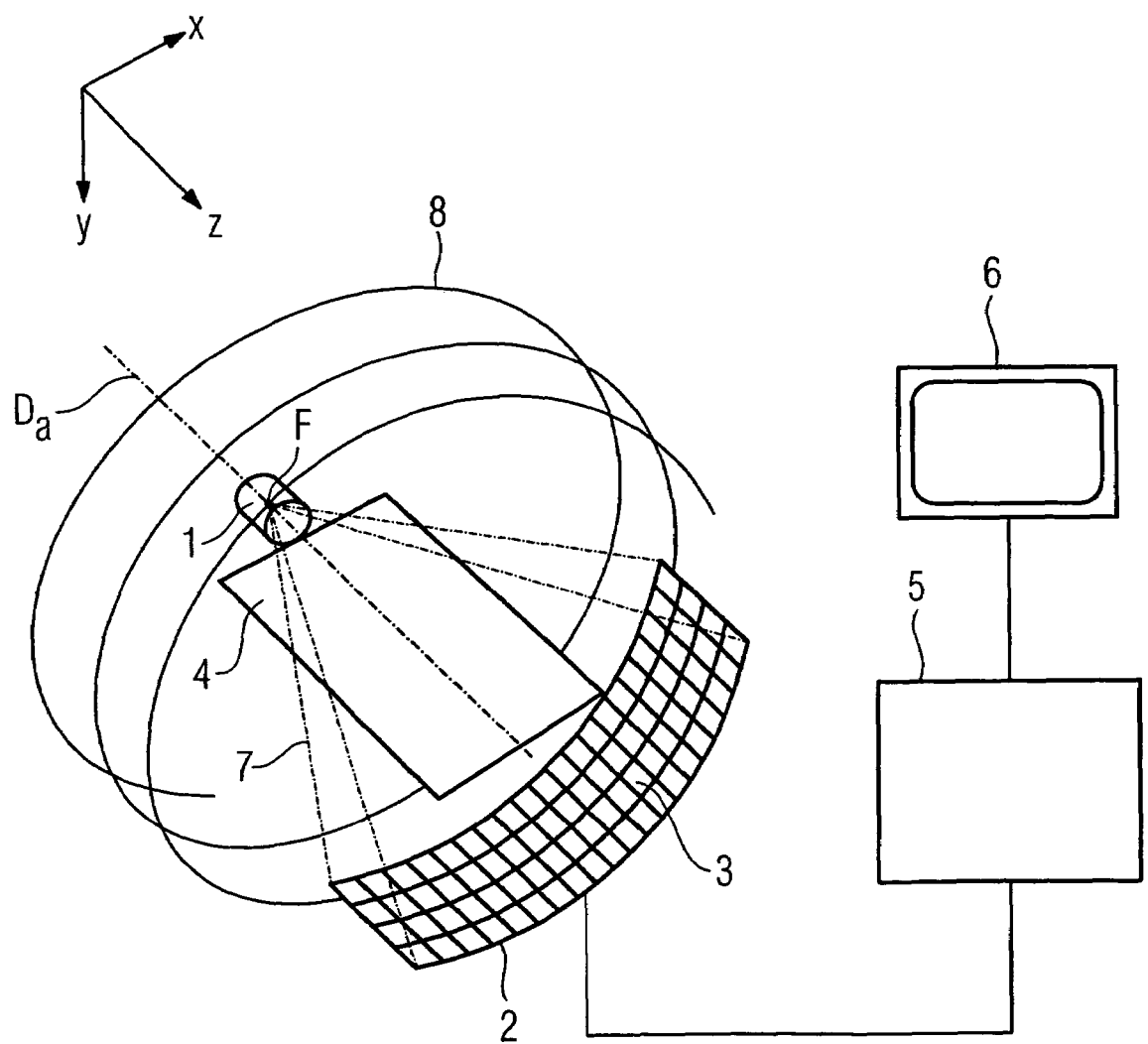
FIG. 1 shows the essential parts of a computed tomography unit in an illustration that is partially like a block diagram and partially in perspective.

A computed tomography unit is shown in FIG. 1 in an illustration that is partially perspective and partially in the form of a block diagram. The computed tomography unit essentially includes a recording system 1, 2 having an X-ray machine 1 and a detector 2 that has detector elements 3 arranged in a detector array to form columns and rows, a computing device 5 for carrying out the method according to at least one embodiment of the invention for the purpose of removing ring artifacts, and a display unit 6 for displaying the result image $E_k$ free from ring artifacts.

The X-ray machine 1 and the detector 2 are fitted opposite one another on a rotary frame (not illustrated) in such a way that during operation of the computed tomography unit an X-ray beam emanating from a focus F of the X-ray machine 1 and bounded by marginal rays 7 impinges on the detector 2.

The rotary frame can be set rotating about a rotation axis $D_a$ by way of a drive device (not illustrated). In this case, the drive axis $D_a$ is parallel to the z-axis of a rectangular three-dimensional coordinate system illustrated in FIG. 1. X-ray pictures can be prepared in this way from different projection directions or positions of angle of rotation for a recording region of, for example, a patient (not illustrated) supported on a patient table 4, for the purpose of reconstructing a number of tomograms $I_k$. The recording region is scanned in this procedure by way of a continuous feed of the patient couch 4 in the direction of the z-axis and in the form of a spiral scan 8 in the case of rotation of the recording system 1, 2 about the recording region to be examined.

Because of the spiral type of scanning, defectively operating or defective detector elements 3 of the detector 2 cause ring artifacts $I_k$ in the respective tomogram $I_k$, which are visible as ring segments and are centered in the image with reference to the center of rotation. The length of the ring segments is a function of the speed with which the recording region is displaced in the direction of the z-axis during scanning per revolution of the recording system 1, 2. In principle, the ring segments are shorter the more rapid the feed of the recording region. For example, it is possible to conceive lengths of ring segments that only have an angular coverage of 10 degrees of a complete circle in the case of rapid scanning.

Figure 2:
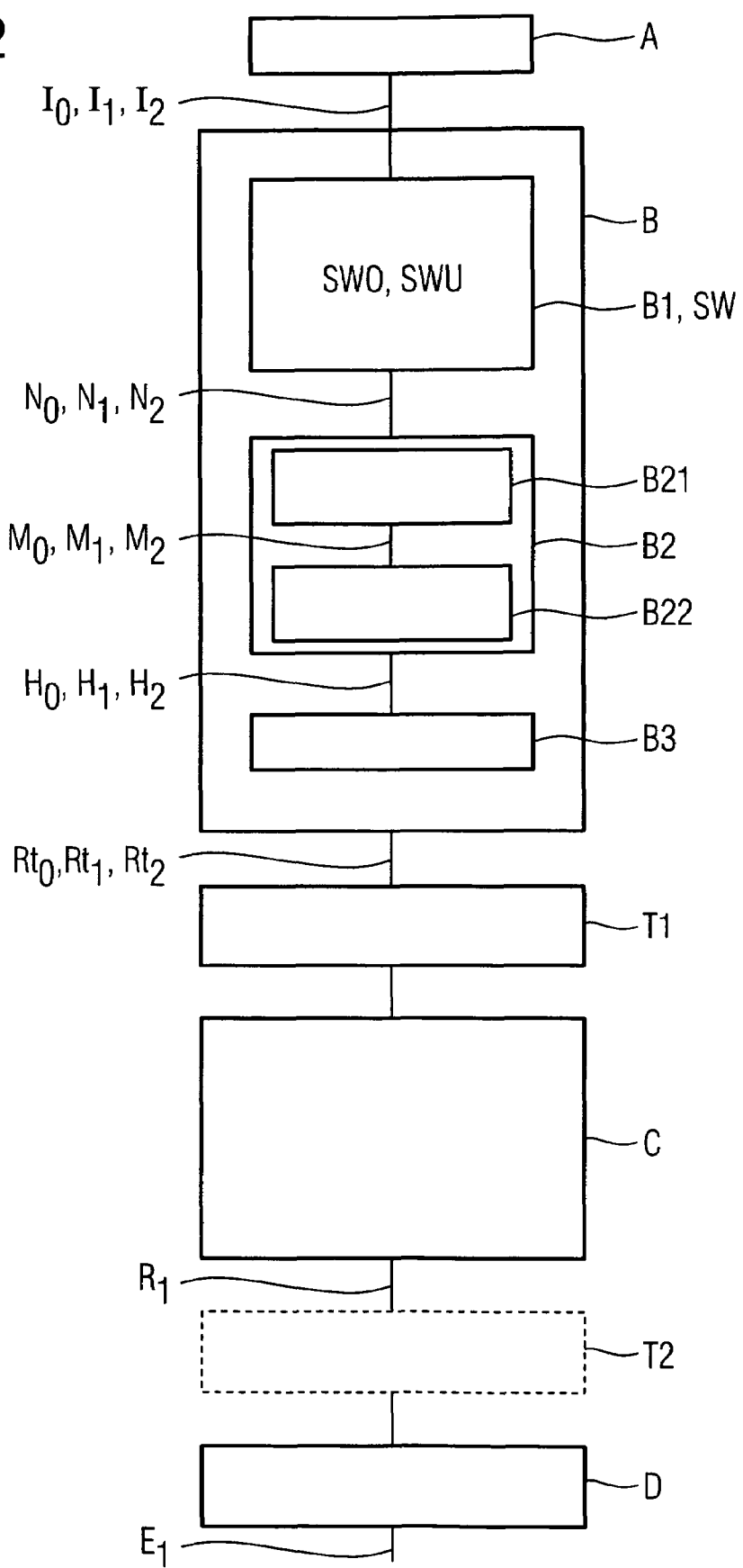
FIG. 2 shows, in outline form, a sequence of a method according to the invention of removing ring artifacts from tomograms with the aid of a computed tomography unit in accordance with FIG. 1.
Figure 3:
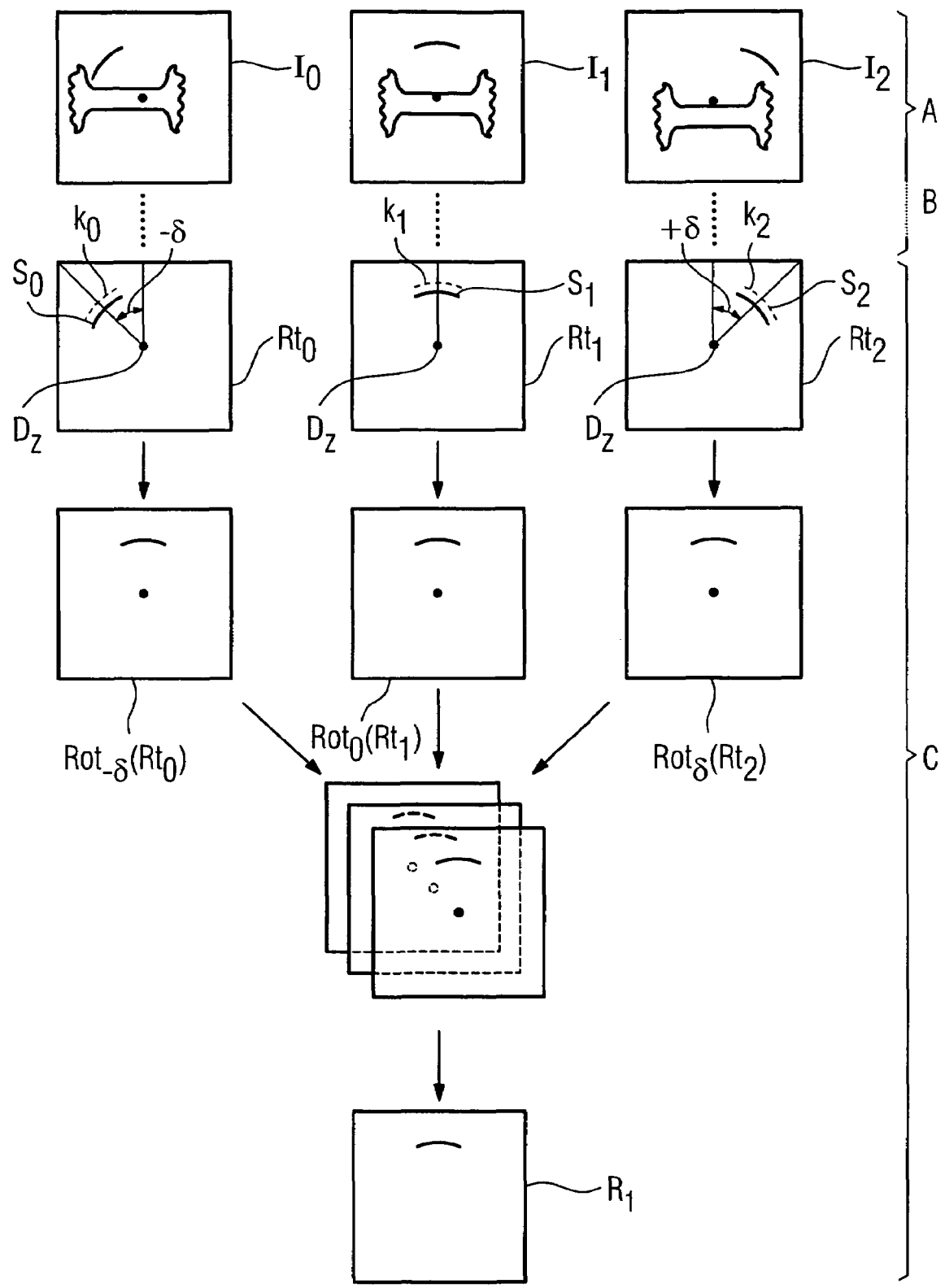
FIG. 3 shows a calculation of a ring artifact image on the basis of 3 temporary ring artifact images.

In conjunction with FIG. 3, FIG. 2 shows the sequence of the method according to at least one embodiment of the invention for the purpose of removing ring artifacts from tomograms, in the form of a flowchart. To simplify the illustration, the method is explained by way of example on the basis of 3 tomograms $I_0$, $I_1$, $I_2$ at the recording position k=1.

The method of at least one example embodiment include the following steps, which are explained in detail below:

First Method Step A:

Reconstructing N, in this example 3 tomograms $I_k$ (k= 0, ... 2) at recording positions 0, 1, 2 that are substantially equidistant in the direction of the rotation axis $D_a$.

Second Method Step B:

Calculating a temporary ring artifact image $Rt_0$ or $Rt_1$ or $Rt_2$ for each tomogram $I_0$ or $I_1$ or $I_2$ that has at least one ring artifact $S_0$ or $S_1$ or $S_2$ present in the respective tomogram $I_0$ or $I_1$ or $I_2$.

Third Method Step C:

Calculating a ring artifact image $R_1$ for the tomogram $I_1$, the ring artifact image $R_1$ being formed by averaging over the three temporary ring artifact images $Rt_0$, $Rt_1$, $Rt_2$, and the temporary ring artifact images $Rt_0$, $Rt_1$, $Rt_2$ being rotated before averaging in such a way that the ring artifacts $S_0$ or $S_1$ or $S_2$ present in the temporary ring artifact images $Rt_0$, $Rt_{1,Rt2}$ substantially coincide and their position substantially corresponds to the ring artifact $S_1$ present in the tomogram $I_1$.

Fourth Method Step D:

Subtracting the ring artifact image $R_1$ from the tomogram $I_1$, in each case one result image $E_1$ being produced in which the ring artifact $S_1$ is removed.

Scanning a recording region, for example by way of the computed tomography unit shown in FIG. 1, is performed in such a way that tomograms $I_0$ or $I_1$ or $I_2$ are reconstructed in the first method step A at substantially equidistant recording positions on the basis of the raw data 3 produced during scanning. Each tomogram $I_0$ or $I_1$ or $I_2$ incldues M*M pixels arranged, for example, in a pixel matrix. Each pixel has a pixel value proportional to an x-radiation acquired by a detector element 3. Each pixel value can be represented in this case with the aid of a bit depth established by the detector 2. Given a bit depth of 12 bits, for example, the pixel values are in a range of between 0 and 4095.

In the present example, the tomograms $I_0$, $I_1$, $I_2$ are to have at least in each case one ring artifact $S_0$ or $S_1$ or $S_2$ that is caused by a defective detector element 3 of the detector 2 during spiral scanning of a recording region. In the present example, it is assumed, furthermore, for the purpose of simplified explanation of the method according to at least one embodiment of the invention that the feed of the recording region in the direction of the rotation axis $D_a$ is constant for each revolution of the recording system 1, 2. The ring artifacts $S_0$, $S_1$, $S_2$ in the tomograms $I_0$, $I_1$, $I_2$ reconstructed substantially at equidistant recording positions 0, 1, 2 are then visible as a ring segment that is rotated by the same angle δ in each case between neighboring tomograms $I_0$, $I_1$ or $I_1$, $I_2$.

After the N tomograms $I_0$, $I_1$, $I_2$ have been reconstructed, a temporary ring artifact image $Rt_0$ or $Rt_1$ or $Rt_2$ that substantially includes only the ring artifact $S_0$ or $S_1$ or $S_2$ is calculated in the second method step B for each tomogram $I_0$ or $I_1$ or $I_2$.

During masking B1 of the tomogram $I_0$ or $I_1$ or $I_2$, the pixel values relating thereto are firstly subjected to threshold value formation SW with an upper threshold SWO and a lower threshold SWU such that the pixel values of image areas of bone and air fractions are limited, and are not falsely detected as ring artifacts during subsequent calculation. The threshold value formation SW is executed in such a way that pixel values that are greater than the upper threshold SWO and could originate from bone fractions are set equal to SWO, while pixel values that are smaller than the lower threshold SWU and could originate from air or air inclusions are set equal to SWU. The upper threshold SWO and the lower threshold SWU depend essentially on a set x-radiation, the dynamics of the detector 2 used and on the maximum attenuation value that can be observed, and can be determined empirically. The masked image $N_0$ or $N_1$ or $N_2$ obtained in each case from this method step has M*M pixels in turn.

Subsequently, high-pass filtering B2 is carried out in the masked image $N_0$ or $N_1$ or $N_2$ in the direction of a center of rotation $D_z$, imaged in the masked image $N_0$ or $N_1$ or $N_2$, of the recording system 1, 2. The high-pass filtering B2 is preferably undertaken in this case by means of median filtering B21 along a multiplicity of straight lines running through the center of rotation $D_z$. The straight lines cover the pixel matrix in such a way that each pixel lies on such a straight line.

A median filter used for median filtering B21 can have, for example, 2*A1+1 (for example A1=3) interpolation points that are respectively arranged symmetrically relative to the pixel respectively to be processed. A spacing present between the interpolation points is selected such that approximately half a line width of the ring artifact $S_0$ or $S_1$ or $S_2$ is covered by the median filter. Such dimensioning of the median filter ensures the detection of the ring artifact $S_0$ or $S_1$ or $S_2$ while other image structures that are larger are advantageously suppressed.

By subtracting B22 a median-filtered image $M_0$ or $M_1$ or $M_2$ obtained in this way from the associated tomogram $I_0$ or $I_1$ or $I_2$, a high-pass-filtered image $H_0$ or $H_1$ or $H_2$ is thus produced that is subjected to an artifact threshold value formation B3 with a lower artifact threshold and an upper artifact threshold. The artifact threshold formation B3 serves the purpose of suppressing image perturbations still possibly present in the image and which can occur in the region of bone edges, for example. Pixels in the high-pass-filtered image $H_0$ or $H_1$ or $H_2$ that have a pixel value greater than the upper artifact threshold or smaller than the lower artifact threshold are identified as perturbations that have falsely been detected as ring artifacts. Such pixels identified as perturbations are limited with reference to their pixel value to the lower or upper artifact threshold such that a temporary ring artifact image $Rt_0$ or $Rt_1$ or $Rt_2$ in which the ring artifact $S_0$ or $S_1$ or $S_2$ is present is produced as a result.

Subsequent to the calculation of the temporary ring artifact image $Rt_0$ or $Rt_1$ or $Rt_2$ relative to the tomogram $I_0$ or $I_1$ or $I_2$, low-pass filtering T1 is undertaken in the image in order to suppress perturbing noise components. The low-pass filtering T1 is performed for each pixel in the temporary ring artifact image $Rt_0$ or $Rt_1$ or $Rt_2$ in the azimuth direction along a multiplicity of circular segments that correspond in each case to a part of a circle seated at the center of rotation of the image, and which have a circular segment length matched to the ring artifact $S_0$ or $S_1$ or $S_2$.

The circular segments cover the pixel matrix in such a way that each pixel lies on such a circular segment. For the sake of clarity, only one circular segment $K_0$ or $K_1$ or $K_2$ is depicted in each case in the temporary ring artifact images in FIG. 3. The low-pass filter T1 can have, for example, 2*A2+1 (for example A2=3) interpolation points that are respectively arranged symmetrically relative to the pixels respectively to be processed along the circular segment $K_0$ or $K_1$ or $K_2$.

A spacing present between the interpolation points is selected such that the low-pass filter T1 covers approximately the length of the ring artifact $S_0$ or $S_1$ or $S_2$. Such a dimensioning of the low-pass filter T1 ensures an adequately effective suppression of high-frequency noise components in the image, while the structures of the ring artifact $S_0$ or $S_1$ or $S_2$ are retained in the image. The low-pass filtering T1 can be implemented, for example, by simple averaging of the pixel values present at the interpolation points. However, it is also possible to conceive other types of low-pass filtering with a transmission characteristic or with another weighting of the interpolation points.

The second method step B is carried out for each tomogram $I_0$ or $I_1$ or $I_2$ such that a temporary ring artifact image $Rt_0$ or $Rt_1$ or $Rt_2$ is produced for each tomogram.

In the example shown in FIG. 2 and FIG. 3, the calculation of a ring artifact image $R_1$ for the tomogram $I_1$ is performed in a third method step C, the ring artifact image $R_1$ being formed by averaging over the previously determined temporary ring artifact images $Rt_0$, $Rt_1$, $Rt_2$, and the temporary ring artifact images $Rt_0$, $Rt_1$, $Rt_2$ being rotated before the averaging in such a way that the ring artifacts $S_0$ or $S_1$ or $S_2$ present in the temporary ring artifact images $Rt_0$, $Rt_1$, $Rt_2$ substantially coincide and their position substantially corresponds to the ring artifact $S_1$ present in the tomogram $I_1$.

A calculation of the ring artifact image $R_1$ at the recording position 1 is shown by way of example in FIG. 3 on the basis of the 3 temporary ring artifact images $Rt_0$, $Rt_1$, $Rt_2$. The temporary ring artifact images $Rt_0$, $Rt_1$, $Rt_2$ respectively contain the ring artifact $S_0$ or $S_1$ or $S_2$, the ring artifacts $S_0$, $S_1$, $S_2$ having the same form. Because of the spiral scanning, the ring artifacts of neighboring temporary ring artifact images $Rt_0$, $Rt_1$ or $Rt_1$, $Rt_2$ do not appear at the same position, but at a position rotated at an angle δ about the center of rotation $D_z$.

As illustrated in the method step C2 in FIG. 3, before the averaging the temporary ring artifact images $Rt_0$, $Rt_1$, $Rt_2$ are rotated in such a way that the ring artifacts $S_0$, $S_1$, $S_2$ come to lie at the same position within the image. The rotation is carried out in this case according to the following calculation rule and can, for example, be carried out on the basis of images illustrated in polar coordinates:

$$R_k = \sum_{l=0}^{2} w_l \cdot Rot_{l\delta}(Rt_{l+k})$$

where l is an index traversing the values 0 to 2, $w_l$ is a weighting factor dependent on the index l, δ is the angular spacing of ring artifacts between two neighboring tomograms, and Rot is a rotation operator that rotates the temporary ring artifact image $Rt_{l+k}$ by the angle l*δ about the center of rotation, the following relationships holding:

$$\sum_{l=0}^{2} w_l = 1$$

and δ=2*n*d/V, and d corresponding to a difference between the neighboring recording positions and V corresponding to feed of the recording system in the direction of the system axis. The factor 1/3, for example, can in each case be used as weighting factors $w_0$, $w_1$, $w_2$.

Following the calculation of the ring artifact image $I_1$, instead of the low-pass filtering T1, illustrated in FIG. 2, in the temporary ring artifact images $Rt_0$, $Rt_1$, $Rt_2$, it is possible to perform an alternative low-pass filtering T2, indicated by dashes in FIG. 2, in the respective final ring artifact image $R_1$. The alternative low-pass filtering T2 in the ring artifact image $R_1$ is undertaken in accordance with the low-pass filtering T1 in the temporary ring artifact image $Rt_0$ or $Rt_1$ or $Rt_2$ in the azimuth direction along a plurality of circular segments that respectively correspond to a part of a circle seated at the center of rotation $D_z$.

In the fourth method step D, a subtraction is carried out between the tomogram $I_1$ and the ring artifact image $R_1$ such that a result image $E_1$ is produced in each case in which the ring artifact is removed.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for removing ring artifacts from tomograms produced with the aid of a computed tomography unit including at least one recording system rotating about a rotation axis, the method comprising:

reconstructing N tomograms $I_k$ (k=1, . . . , N) at recording positions that are substantially equidistant in the direction of the rotation axis;

calculating a temporary ring artifact image $Rt_k$ for each tomogram $I_k$ which has at least one ring artifact present in the respective tomogram $I_k$;

calculating a ring artifact image $R_k$ for each tomogram $I_k$, the respective ring artifact image $R_k$ being formed by averaging over at least a portion $T_{sub}$ of the temporary ring artifact images $Rt_k$, and the temporary ring artifact images $Rt_k$ being rotated before averaging in such a way that the ring artifacts present in the temporary artifact images $Rt_k$ substantially coincide and their position substantially corresponds to the ring artifacts present in the tomogram $I_k$; and subtracting the respective ring artifact image $R_k$ from the respective tomogram $I_k$, in each case one result image $E_k$ being produced in which the ring artifact is removed.

2. The method as claimed in claim 1, wherein the calculation of a temporary ring artifact image $Rt_k$ comprises:

masking bone and air fractions in the respective tomogram $I_k$ such that a masked image $N_k$ is respectively produced for each tomogram $I_k$, subjecting the respective masked image $N_k$ to high-pass filtering in the radial direction relative to the center of rotation in the masked image $N_k$ such that a high-pass-filtered image $H_k$ is produced for each masked image $N_k$, and artifact threshold value formation in the respective high-pass-filtered image $H_k$ with a negative artifact threshold and a positive artifact threshold, so as to produce for each high-pass-filtered image $H_k$ the temporary ring artifact image $Rt_k$ that has the ring artifacts present in the respective tomogram $I_k$.

3. The method as claimed in claim 2, wherein the masking of bone and air fractions comprises:

setting all the image values greater than an upper threshold SWO equal to SWO, and setting all the image values smaller than a lower threshold SWU equal to SWU such that a masked image $N_k$ is produced.

4. The method as claimed in claim 2, wherein the high-pass filtering comprises:

carrying out median filtering in radial directions, running through the center of rotation, in the masked image $N_k$ such that a median-filtered image $M_k$ is produced, and subtracting the median-filtered image $M_k$ from the tomogram $I_k$ such that a high-pass-filtered image $H_k$ is produced.

5. The method as claimed in claim 1, wherein the method includes, before the calculation of the ring artifact image $R_k$:

carrying out low-pass filtering in the respective temporary ring artifact image $Rt_k$ in the azimuth direction along at least one circular segment that corresponds to a part of a circle seated at the center of rotation and which has a circular segment length matched to the ring artifact.

6. The method as claimed in claim 1, wherein after the calculation of the ring artifact image $R_k$, the method includes:

carrying out low-pass filtering in the ring artifact image $R_k$ in the azimuth direction along at least one circular segment that corresponds to a part of a circle seated at the center of rotation and which has a circular segment length matched to the ring artifact.

7. The method as claimed in claim 1, wherein the calculation of the ring artifact image $R_k$ is performed using the following calculation rule:

$$R_k = \sum_{l=-T}^{+T} w_l \cdot Rot_{l \cdot \delta}(Rt_{l+k}),$$

where l is an index traversing the values −T and +T, $w_l$ is a weighting factor dependent on the index l, δ is the angular spacing of ring artifacts between two neighboring tomograms, and Rot is a rotation operator that rotates the temporary ring artifact image $Rt_{l+k}$ by the angle l*δ about the center of rotation, the following relationships holding:

$$T_{sub} = 2*T + l, \quad \sum_{l=-T}^{T} w_l = 1$$

and δ=2*n*d/V, and d corresponding to a difference between the neighboring recording positions and V corresponding to feed of the recording system in the direction of the system axis.

8. The method as claimed in claim 7, wherein the following holds for the weighting factors $w_l$: $w_l = 1/T_{sub}$.

9. The method as claimed in claim 1, wherein at least some of the method steps are carried out in polar coordinates with an origin of coordinates seated at the center of rotation of the images.

10. A computed tomography unit that is designed for carrying out the method as claimed in claim 1.

11. The method as claimed in claim 3, wherein the high-pass filtering comprises:

carrying out median filtering in radial directions, running through the center of rotation, in the masked image $N_k$ such that a median-filtered image $M_k$ is produced, and subtracting the median-filtered image $M_k$ from the tomogram $I_k$ such that a high-pass-filtered image $H_k$ is produced.

12. The method as claimed in claim 2, wherein the method includes, before the calculation of the ring artifact image $R_k$:

carrying out low-pass filtering in the respective temporary ring artifact image $Rt_k$ in the azimuth direction along at least one circular segment that corresponds to a part of a circle seated at the center of rotation and which has a circular segment length matched to the ring artifact.

13. The method as claimed in claim 3, wherein the method includes, before the calculation of the ring artifact image $R_k$:

carrying out low-pass filtering in the respective temporary ring artifact image $Rt_k$ in the azimuth direction along at least one circular segment that corresponds to a part of a circle seated at the center of rotation and which has a circular segment length matched to the ring artifact.

14. The method as claimed in claim 11, wherein the method includes, before the calculation of the ring artifact image $R_k$:

carrying out low-pass filtering in the respective temporary ring artifact image $Rt_k$ in the azimuth direction along at least one circular segment that corresponds to a part of a circle seated at the center of rotation and which has a circular segment length matched to the ring artifact.

15. The method as claimed in claim 5, wherein after the calculation of the ring artifact image $R_k$, the method includes:

carrying out low-pass filtering in the ring artifact image $R_k$ in the azimuth direction along at least one circular segment that corresponds to a part of a circle seated at the center of rotation and which has a circular segment length matched to the ring artifact.

16. The method as claimed in claim 14, wherein after the calculation of the ring artifact image $R_k$, the method includes: carrying out low-pass filtering in the ring artifact image $R_k$ in the azimuth direction along at least one circular segment that corresponds to a part of a circle seated at the center of rotation and which has a circular segment length matched to the ring artifact.

17. The method as claimed in claim 2, wherein the calculation of the ring artifact image $R_k$ is performed using the following calculation rule:

$$R_k = \sum_{l=-T}^{+T} w_l \cdot Rot_{l \cdot \delta}(Rt_{l+k}),$$

where l is an index traversing the values −T and +T, $w_l$ is a weighting factor dependent on the index l, $\delta$ is the angular spacing of ring artifacts between two neighboring tomograms, and Rot is a rotation operator that rotates the temporary ring artifact image $Rt_{l+k}$ by the angle $1*\delta$ about the center of rotation, the following relationships holding:

$$T_{sub} = 2*T + l, \quad \sum_{l=-T}^{T} w_l = 1$$

and $\delta = 2*n*d/V$, and d corresponding to a difference between the neighboring recording positions and V corresponding to feed of the recording system in the direction of the system axis.

18. The method as claimed in claim 17, wherein the following holds for the weighting factors $w_l$: $w_l = 1/T_{sub}$.

19. A device for removing ring artifacts from tomograms produced with the aid of a computed tomography unit including at least one recording system rotating about a rotation axis, the device comprising:

means for reconstructing N tomograms $I_k$ (k=1, ..., N) at recording positions that are substantially equidistant in the direction of the rotation axis;

means for calculating a temporary ring artifact image $Rt_k$ for each tomogram $I_k$ which has at least one ring artifact present in the respective tomogram $I_k$;

means for calculating a ring artifact image $R_k$ for each tomogram $I_k$, the respective ring artifact image $R_k$ being formed by averaging over at least a portion $T_{sub}$ of the temporary ring artifact images $Rt_k$, and the temporary ring artifact images $Rt_k$ being rotated before averaging in such a way that the ring artifacts present in the temporary artifact images $Rt_k$ substantially coincide and their position substantially corresponds to the ring artifacts present in the tomogram $I_k$; and means for subtracting the respective ring artifact image $R_k$ from the respective tomogram $I_k$, in each case one result image $E_k$ being produced in which the ring artifact is removed.

20. A computer readable medium including program segments for, when executed on a computer, causing the computer to implement the method of claim 1.

* * * * *